United States Patent
Suzuki et al.

(10) Patent No.: US 11,261,275 B2
(45) Date of Patent: Mar. 1, 2022

(54) PROTEIN STABILIZER AND PROTEIN STABILIZATION REAGENT

(71) Applicant: NOF Corporation, Tokyo (JP)

(72) Inventors: Hirotaka Suzuki, Kawasaki (JP); Takashi Sasaki, Kawasaki (JP); Nobuyuki Sakamoto, Kawasaki (JP)

(73) Assignee: NOF Corporation, Tokyo (JP)

( * ) Notice: Subject to any disclaimer, the term of this patent is extended or adjusted under 35 U.S.C. 154(b) by 122 days.

(21) Appl. No.: 16/616,656

(22) PCT Filed: May 18, 2018

(86) PCT No.: PCT/JP2018/019368
§ 371 (c)(1),
(2) Date: Nov. 25, 2019

(87) PCT Pub. No.: WO2018/216628
PCT Pub. Date: Nov. 29, 2018

(65) Prior Publication Data
US 2020/0102415 A1    Apr. 2, 2020

(30) Foreign Application Priority Data
May 25, 2017 (JP) .............................. JP2017-103514

(51) Int. Cl.
*C08F 230/02* (2006.01)
*C08F 220/28* (2006.01)
*C08F 220/18* (2006.01)

(52) U.S. Cl.
CPC ........ *C08F 220/282* (2020.02); *C08F 230/02* (2013.01); *C08F 220/18* (2013.01)

(58) Field of Classification Search
CPC ................. C08F 230/02; C08F 220/18; C08F 220/1802; C08F 220/1803; C08F 220/1804; C08F 220/1806; C08F 220/1807; C08F 220/1808; C08F 220/1809; C08F 220/1811; C08F 220/1812; C08F 220/1818; C08F 220/20
See application file for complete search history.

(56) References Cited

FOREIGN PATENT DOCUMENTS

| | | | |
|---|---|---|---|
| JP | 10045794 A | * | 2/1998 |
| JP | H10-45794 A | | 2/1998 |
| JP | 2004-108850 A | | 4/2004 |
| JP | 2006-305401 A | | 11/2006 |
| JP | 2007-054516 A | | 3/2007 |
| JP | 2007054516 A | * | 3/2007 |
| JP | 2008-105358 A | | 5/2008 |
| JP | 2008105358 A | * | 5/2008 |

OTHER PUBLICATIONS

Cleland et al., "Polyethylene Glycol Enhanced Refolding of Bovine Carbonic Anhydrase B," The Journal of Biological Chemistry, vol. 267, No. 19, Jul. 5, 1992, pp. 13327-13334.
Shiraki et al., "Biophysical Effect of Amino Acids on the Prevention of Protein Aggregation," J. Biochem., vol. 132, No. 4, 2002, pp. 591-595.

* cited by examiner

*Primary Examiner* — Ling Siu Choi
*Assistant Examiner* — David L Miller
(74) *Attorney, Agent, or Firm* — Amster, Rothstein & Ebenstein LLP

(57) ABSTRACT

There is provided a protein stabilizer for stably storing a protein in a solution. The protein may be an enzyme, an antibody, an enzyme-labeled antibody, or the like for a biochemical assay, etc. There is further provided a protein stabilization reagent comprising a protein-containing solution and the protein stabilizer dissolved therein. The protein stabilizer comprises a copolymer prepared by copolymerizing a monomer (a) of the following formula (1), a monomer (b) of the following formula (2), and a monomer (c) of the following formula (3).

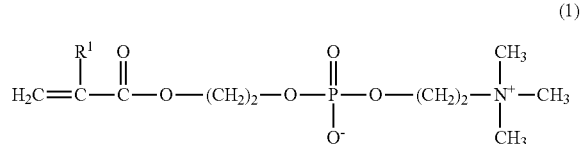

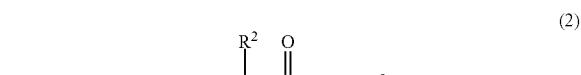

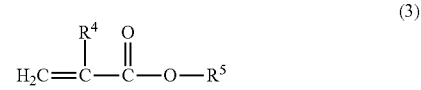

2 Claims, No Drawings

PROTEIN STABILIZER AND PROTEIN STABILIZATION REAGENT

CROSS-REFERENCE TO RELATED APPLICATIONS

This application is a U.S. national stage entry under 35 USC § 371 of PCT International Patent Application No. PCT/JP2018/019368, filed May 18, 2018, which claims priority to Japanese Patent Application No. 2017-103514, filed May 25, 2017, the contents of which are incorporated herein by reference in their entirety.

FIELD OF ART

The present invention relates to a protein stabilizer, and further relates to a protein stabilization reagent containing a protein-containing solution and the protein stabilizer dissolved therein.

BACKGROUND ART

Biochemical assays, such as enzyme immunoassays, turbidimetric immunoassays, latex agglutination assays, immunochromatographic assays, nucleic acid assays, and immunostaining assays, have been widely used in the fields of clinical examinations, in-vitro diagnostics, and companion diagnostics. Furthermore, in recent years, the technologies of the assays have been widely used for food analyses and environment analyses.

The above diagnostics and analyses must be carried out accurately. Therefore, in a case where a protein such as an enzyme, an antibody, or a labeled antibody is used as a component of a reagent for the diagnostics and analyses, it is important that the protein can stably maintain its bioactivity or the like for a long period of time. Furthermore, also in a case where a protein such as an enzyme or an antibody is used as an assay target (specimen) in the above assays, the protein needs to be stably stored.

More specifically, in the case where the protein is used as the component of the reagent, the protein is required to have a sufficient stability while the reagent is stored at room temperature or refrigeration temperature. The sufficient stability at the room temperature may be such that the reagent can maintain the activity during a time from the preparation of the reagent to the start of the biochemical assay or during a standby time in an autoanalyzer for treating many specimens. The stability at the refrigeration temperature may be a stability during a long-term storage of the reagent or during an on-board storage of the reagent in an autoanalyzer. Furthermore, in the case where the protein is used as the assay target, the protein is required to have the same sufficient stability while a solution containing the protein is under the above conditions.

Thus, the stabilization of the protein is very important. Nevertheless, most of the proteins may be readily denatured or deactivated due to various factors such as heating, refrigeration, freezing, light, pH, salt concentration, oxidation, non-specific adsorption to container, and self-aggregation.

In the autoanalyzer, it is preferred that the reagent or the assay target is in the state of a solution from the viewpoint of easy handling. However, it is known that the protein dissolved in the solution exhibits an extremely lower long-term stability as compared with the protein in the dry state with almost no water.

In a commonly known method for stabilizing the solution containing the protein, a bovine serum albumin (hereinafter referred to as BSA) is added to the solution. However, this method fails to achieve a satisfactory stabilization effect. In addition, this method has various problems of high risk of infection such as mad cow disease, large lot-to-lot nonuniformity of natural product (low reproducibility), coagulation sedimentation of BSA during long-term storage, etc.

Therefore, Patent Literature 1 discloses an amino acid ester or a polyamine, Patent Literature 2 discloses a phosphorylcholine-containing copolymer, Non-Patent Literature 1 discloses an amino acid, and Non-Patent Literature 2 discloses a polyethylene glycol, as a component used instead of the BSA in a protein-containing solution. Furthermore, also known is a method containing dissolving a sugar such as sucrose, lactose, or trehalose in a protein-containing solution to improve the protein stabilization effect.

CITATION LIST

Patent Publication 1: JP 2004-108850 A
Patent Publication 2: JP 1998-45794 A
Non-Patent Literature 1: K. Shiraki, et. al., J. Biochem., 132, 591-595 (2002)
Non-Patent Literature 2: Cleland J L, et. al., J. Biol. Chem., 267, 13327-13334 (1992)

SUMMARY OF THE INVENTION

Problems to be Solved by the Invention

However, a satisfactory protein stabilization effect cannot be achieved by the above-described methods. In addition, in the method containing dissolving the sugar such as sucrose in the protein-containing solution, the viscosity of the solution may be increased, and the handling of the solution may be deteriorated. Thus, it is very difficult to satisfactorily stabilize the protein in the solution while preventing the viscosity increase of the solution.

Accordingly, an object of the present invention is to provide a protein stabilizer and a protein stabilization reagent for stably storing a protein in a solution, the protein being an enzyme, an antibody, an enzyme-labeled antibody, or the like for a biochemical assay, etc.

Means for Solving the Problem

As a result of intense research in view of the above object, the inventors have found that a particular copolymer is capable of highly stabilize a protein in a solution. The present invention has been accomplished based on this finding.

According to an aspect of the present invention, there is provided a protein stabilizer comprising a copolymer prepared by copolymerizing a monomer (a) of the following formula (1), a monomer (b) of the following formula (2), and a monomer (c) of the following formula (3).

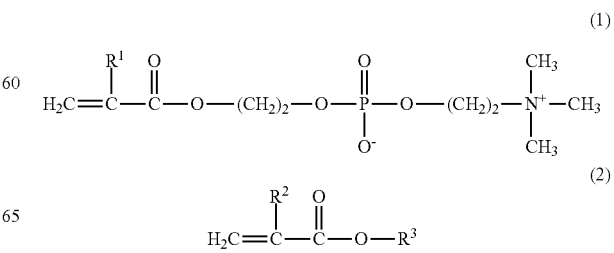

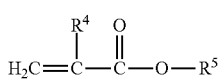

In the formula (1), $R^1$ is a hydrogen atom or a methyl group. In the formula (2), $R^2$ is a hydrogen atom or a methyl group, and $R^3$ is an alkyl group that contains 3 to 6 carbon atoms and has 2 or more hydroxyl groups. In the formula (3), $R^4$ is a hydrogen atom or a methyl group, and $R^5$ is an alkyl group containing 2 to 18 carbon atoms.

According to another aspect of the present invention, there is provided a protein stabilization reagent comprising a protein, water, and the above protein stabilizer, wherein the content of the protein stabilizer is 0.01% to 5.0% by mass in the reagent.

Effect of the Invention

The protein stabilizer and the protein stabilization reagent of the present invention are capable of stably storing a protein in a solution at room temperature or lower temperature for a long period of time. The protein may be an enzyme, an antibody, an enzyme-labeled antibody, or the like for a biochemical assay, etc. In addition, in a case where a sugar such as sucrose is added to the protein stabilization reagent, the protein stabilization effect of the reagent can be improved only by adding a small amount of the sugar, so that viscosity increase of the reagent can be prevented.

EMBODIMENTS OF THE INVENTION

The protein stabilizer of the present invention contains a copolymer prepared by copolymerizing a monomer (a) represented by the following formula (1), a monomer (b) represented by the following formula (2), and a monomer (c) represented by the following formula (3).

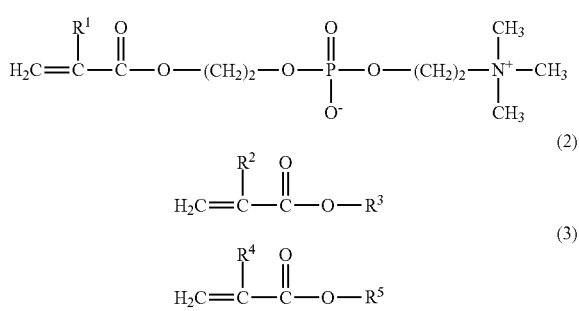

In the formula (1), $R^1$ is a hydrogen atom or a methyl group. It is preferred that $R^1$ is the methyl group from the viewpoint of availability of starting materials.

In the formula (2), $R^2$ is a hydrogen atom or a methyl group. It is preferred that $R^2$ is the methyl group from the viewpoint of stability.

In the formula (2), $R^3$ is an alkyl group that contains 3 to 6 carbon atoms and has 2 or more hydroxyl groups. It is preferred that $R^3$ is an alkyl group that contains 3 to 5 carbon atoms and has 2 to 4 hydroxyl groups from the viewpoint of availability.

Specific examples of the monomers (b) of the formula (2) include glycerin mono(meth)acrylates, threitol mono(meth) acrylates, erythritol mono(meth)acrylates, xylitol mono (meth)acrylates, arabitol mono(meth)acrylates, mannitol mono(meth)acrylates, galactitol mono(meth)acrylates, and sorbitol mono(meth)acrylates. In particular, the glycerin mono(meth)acrylates and the xylitol mono(meth)acrylates are preferred. In the present invention, the term "(meth) acrylate" means "acrylate and/or methacrylate".

In the formula (3), $R^4$ is a hydrogen atom or a methyl group. It is preferred that $R^4$ is the methyl group from the viewpoint of stability.

In the formula (3), $R^5$ is an alkyl group containing 2 to 18 carbon atoms. The alkyl group of $R^5$ does not have a substituent such as a hydroxyl group.

Specific examples of the monomers (c) of the formula (3) include ethyl (meth)acrylate, propyl (meth)acrylate, butyl (meth)acrylate, pentyl (meth)acrylate, hexyl (meth)acrylate, heptyl (meth)acrylate, octyl (meth)acrylate, nonyl (meth) acrylate, decyl (meth)acrylate, undecyl (meth)acrylate, dodecyl (meth)acrylate, tridecyl (meth)acrylate, tetradecyl (meth)acrylate, pentadecyl (meth)acrylate, cetyl (meth)acrylate, heptadecyl (meth)acrylate, and stearyl (meth)acrylate. In particular, the butyl methacrylate, lauryl methacrylate, and stearyl methacrylate are preferred. In the present invention, the term "(meth)acrylate" means "acrylate and/or methacrylate", and the term "(meth)acrylic" means "acrylic and/or methacrylic".

When total 100% by mole of the monomer (a), the monomer (b), and the monomer (c) are used in the copolymerization, it is preferred that the ratio of the monomer (a) is 10% to 80% by mole, the ratio of the monomer (b) is 10% to 80% by mole, and the ratio of the monomer (c) is 10% to 80% by mole. From the viewpoint of improvement of the protein stabilization effect, it is more preferred that the ratio of the monomer (a) is 40% to 50% by mole, the ratio of the monomer (b) is 20% to 40% by mole, and the ratio of the monomer (c) is 20% to 40% by mole.

The copolymer prepared by copolymerizing the monomers (a) to (c) is a ternary copolymer containing structural units of the following formulae (4) to (6). $R^1$ to $R^5$ in the formulae (4) to (6) have the same meanings and the same preferred embodiments as those in the formulae (1) to (3). The copolymer may have a terminal structure depending on a polymerization method to be hereinafter described. The copolymer may contain a small amount of an undesired branched structure or by-product structure depending on a specificity of a polymerization reaction. The copolymer may contain inevitable impurities.

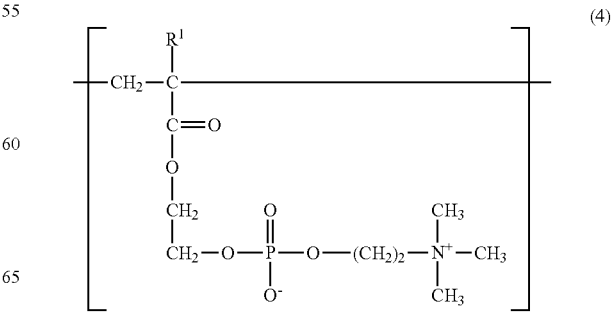

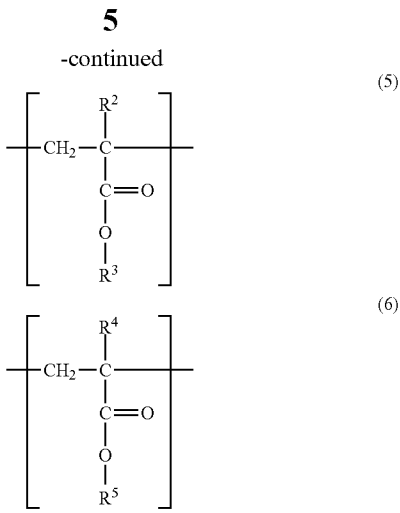

The ratios of the structural units of the formulae (4) to (6) in the copolymer corresponds to the ratios of the monomers (a) to (c) used in the copolymerization. When the copolymer contains total 100% by number of the structural units of the formulae (4) to (6), it is preferred that the ratio of the structural unit of the formula (4) is 10% to 80%, the ratio of the structural unit of the formula (5) is 10% to 80%, and the ratio of the structural unit of the formula (6) is 10% to 80%. It is more preferred that the ratio of the structural unit of the formula (4) is 40% to 50%, the ratio of the structural unit of the formula (5) is 20% to 40%, and the ratio of the structural unit of the formula (6) is 20% to 40%. It should be noted that the ratio of moieties such as the terminal structure other than the structural units the formulae (4) to (6) is vanishingly low in the copolymer.

In the protein stabilizer of the present invention, the copolymer prepared by copolymerizing the monomers (a) to (c) may have any structure such as a random copolymer structure, a block copolymer structure, or a mixture thereof.

The weight-average molecular weight (Mw) of the copolymer, which is obtained by a gel filtration chromatography analysis in terms of polyethylene glycol, is 1,000 to 700,000, preferably 5,000 to 500,000, more preferably 10,000 to 250,000, particularly preferably 50,000 to 150,000. When the weight-average molecular weight is within the above range, an excellent protein stabilization effect can be achieved. For example, the gel filtration chromatography analysis may be carried out using a high-performance liquid chromatography system of CCPS 8020 series (available from Tosoh Corporation).

The copolymerization method for preparing the copolymer may be a known method such as a solution polymerization method, a bulk polymerization method, an emulsion polymerization method, or a suspension polymerization method. For example, the monomers (a) to (c) may be polymerized in the presence of a polymerization initiator in a solvent via a polymerization reaction such as a radical polymerization reaction.

The initiator for the polymerization reaction may be selected from common initiators. For example, an aliphatic azo compound or an organic peroxide may be used as the initiator in the radical polymerization. Specific examples of the initiators include 2,2'-azobisisobutyronitrile, benzoyl peroxide, diisopropyl peroxydicarbonate, t-butyl peroxy-2-ethylhexanoate, t-butyl peroxypivalate, t-butyl peroxydiisobutyrate, and persulfate salts such as potassium persulfate and ammonium persulfate. A mixture of two or more of the initiators may be used in the polymerization reaction. A redox-type radical promoter may be used in the polymerization reaction.

The polymerization temperature is preferably 30° C. to 80° C., more preferably 40° C. to 70° C. The polymerization time is preferably 2 to 72 hours. When the polymerization temperature and the polymerization time are within the ranges, the polymerization reaction can be desirably carried out. A solvent may be used to smoothly carry out the polymerization reaction. Examples of the solvents include water, methanol, ethanol, propanol, t-butanol, benzene, toluene, dimethylformamide, tetrahydrofuran, dioxane, chloroform, and mixtures thereof.

The protein, which is stabilized by the protein stabilizer of the present invention, is not particularly limited. Examples of the proteins include antibodies (such as immunoglobulin G and immunoglobulin E), enzymes (such as peroxidases, alkaline phosphatases, β-D-galactosidases, lipases, DNA polymerases, RNA polymerases, and reverse transcriptases), and complexes of an antibody and an enzyme (such as enzyme-labeled antibodies). Among the proteins, the protein stabilizer can be suitably used for stabilizing the enzyme-labeled antibodies, which have been widely used in enzyme immunoassay methods.

When the protein coexists with the protein stabilizer of the present invention in the solution, the protein stabilizer can prevent the deactivation of the protein and can maintain the bioactivity of the protein for a long period of time. It is preferred that the protein stabilizer of the present invention is dissolved in water, and the protein is dissolved and stored in the aqueous solution.

Only the protein and the protein stabilizer of the present invention may be dissolved in the aqueous solution. A buffering agent may be further dissolved in the aqueous solution. Thus, a buffer solution, which have been commonly used in this field, may be used as a solvent for dissolving the protein and the protein stabilizer of the present invention. Examples of the buffer solutions include phosphate buffers, Tris buffers, Good buffers, glycine buffers, boric-acid buffers, and carbonate buffers. A mixture of the buffer solutions may be used as the solvent.

In the aqueous solution, the concentration of the protein stabilizer of the present invention is preferably 0.01% to 5.0% by mass. When the concentration is within this range, an excellent protein stabilization effect can be achieved. The preferred concentration range of the protein to be stabilized largely depends on the type of the assay target protein. Therefore, the concentration of the protein may be appropriately selected depending on the assay target protein.

The temperature, at which the protein is stabilized, is preferably –30° C. to 40° C., particularly preferably 0° C. to 30° C. Thus, when the protein coexists with the protein stabilizer of the present invention in the solution at a temperature within this range, the protein can be stabilized and stably stored for a long period of time.

The protein stabilization reagent of the present invention is a solution containing the protein, water, and the protein stabilizer of the present invention. The solution contains 0.01% to 5.0% by mass of the protein stabilizer. The protein stabilization reagent is preferably an aqueous solution containing the protein and the protein stabilizer in the water. The water is preferably a purified water, a pure water, an ion-exchange water, or the like.

The protein contained in the protein stabilization reagent is a protein that can be stabilized by the protein stabilizer. The preferred concentration of the protein in the protein stabilization reagent depends largely on the type of the protein, etc. It is preferred that the concentration of the protein to be stabilized is controlled depending on the type of the protein or the intended use of the reagent, e.g. within the range of $10^{-15}$ to 1% by mass.

As described above, the protein stabilizer of the present invention can be used in a common buffer solution as long as a bioactivity such as an enzymatic activity, an antibody activity, or an antigenicity of the protein is not deteriorated therein. Thus, the protein stabilization reagent may contain the protein, the water, the protein stabilizer of the present invention, and the buffer solution. Alternatively, the protein stabilization reagent may be prepared by dissolving the protein and the protein stabilizer in the buffer solution.

Examples of the buffer solutions usable together with the protein stabilizer include phosphate buffers, Tris-HCl buffers, Good buffers, glycine buffers, boric-acid buffers, and carbonate buffers.

The protein stabilizer may be used together with another agent, compound, or the like common in this field, as long as it does not interfere with the effects of the present invention. Thus, the protein stabilization reagent of the present invention may contain such an agent, compound, or the like in addition to the protein, the water, and the protein stabilizer of the present invention. Examples of the agents and compounds include polyols, polyethers, proteins other than the stabilization target protein, salts, surfactants, biochemical agents, preservatives, and organic solvents. The polyols include glycerol, sucrose, and glucose. The polyethers include polyoxyethylene glycols. The proteins other than the stabilization target protein include serum albumins, gelatins, and caseins. The salts include salts of amino acids (such as glycine, alanine, glutamic acid, aspartic acid, lysine, and histidine), peptides, inorganic salts (such as sodium salts, potassium salts, magnesium salts, calcium salts, phosphate salts, sulfate salts, and hydrochloride salt), and organic salts (such as salts of tris(hydroxyethyl)aminomethane, ethylenediaminetetraacetic acid, acetic acid, citric acid, and malic acid). The surfactants include polyoxyethylene alkyl ethers, polyoxyethylene sorbitan monoalkyl ethers, and alkylbetaines. The biochemical agents include flavin agents, coenzyme agents (such as colipases), and nucleic acid agents (such as nucleosides and nucleotides). The preservatives include sodium azide, p-oxybenzoic acid formulations, dehydroacetic acid formulations, and Proclin formulations. The organic solvents include methanol, ethanol, n-propanol, isopropanol, isoamyl alcohol, dimethylformamide, dimethyl sulfoxide, tetrahydrofuran, chloroform, and phenol.

As described above, the temperature, at which the protein stabilizer of the present invention is used, is preferably −30° C. to 40° C., more preferably 0° C. to 30° C., from the viewpoint of the protein stabilization effect. Therefore, also the temperature, at which the protein stabilization reagent of the present invention is stored, is preferably −30° C. to 40° C., more preferably 0° C. to 30° C. In a case where the protein stabilization reagent is stored at a temperature of 0° C. or lower, it is preferred that an organic solvent having an antifreezing effect (e.g. glycerol) is added to the reagent.

EXAMPLES

The present invention will be described more specifically below with reference to Examples without intention of restricting the invention.
<Synthesis of Copolymer>
As described in Synthesis Examples 1 to 4, copolymers 1 and 2 were synthesized as protein stabilizers according to the present invention, and copolymers 3 and 4 were synthesized as protein stabilizers of Comparative Examples. In Synthesis Examples 1 to 4, the following monomers were used.

Monomer (a): 2-methacryloyloxyethyl phosphorylcholine (hereinafter referred to as MPC)
Monomer (b): glycerin monomethacrylate (hereinafter referred to as GLM)
Monomer (c): n-butyl methacrylate (hereinafter referred to as BMA)
Monomer (x): methacrylic acid (hereinafter referred to as MAc, a monomer different from the monomers (a) to (c))

Synthesis Example 1 (Synthesis of Copolymer 1)

8.4 g of MPC, 4.5 g of GLM, and 2.1 g of BMA were weighed and introduced into a glass flask for polymerization. 0.147 g of 2,2'-azobisisobutyronitrile (hereinafter referred to as AIBN) was added thereto as a polymerization initiator, and 42.5 g of a purified water and 42.5 g of ethanol were further added thereto as polymerization solvents. Thus, the mole ratio of the monomers MPC/GLM/BMA was 40/40/20. The internal air in the reaction container was sufficiently replaced with nitrogen, and then the monomers were polymerized under heating at 55° C. for 5 hours. The resultant reaction liquid was cooled with ice, and was added to diethyl ether dropwise to precipitate the product. The precipitate was isolated by filtration, washed with diethyl ether, and dried under vacuum, to obtain a white powder of the copolymer 1.

The obtained copolymer 1 was dissolved in a phosphate buffered saline, and the resultant solution was subjected to an analysis using a gel filtration chromatography (hereinafter referred to as GFC). As a result, the copolymer 1 had a weight-average molecular weight of 98,000 in terms of polyethylene glycol. The GFC analysis was carried out under the following conditions.

System: high-performance liquid chromatography system of CCPS 8020 series (available from Tosoh Corporation)
Column: SB-802.5 HQ and SB-806MN HQ connected in series
Eluent: 20-mM phosphate buffer
Detector: RI and UV (wavelength 210 nm)
Flow rate: 0.5 mL/minute
Measurement time: 70 minutes
Injection volume: 100 μL
Polymer concentration: 0.1% by weight
Column oven temperature: 45° C.

Synthesis Example 2 (Synthesis of Copolymer 2)

11.4 g of MPC, 3.1 g of GLM, and 5.5 g of BMA were weighed and introduced into a glass flask for polymerization. 0.730 g of AIBN was added thereto as a polymerization initiator, and 40.0 g of a purified water and 40.0 g of ethanol were further added thereto as polymerization solvents. Thus, the mole ratio of the monomers MPC/GLM/BMA was 40/20/40. The internal air in the reaction container was sufficiently replaced with nitrogen, and then the monomers were polymerized under heating at 55° C. for 5 hours. The resultant reaction liquid was cooled with ice, and was added to diethyl ether dropwise to precipitate the product. The precipitate was isolated by filtration, washed with diethyl ether, and dried under vacuum, to obtain a white powder of the copolymer 2.

The obtained copolymer 2 was dissolved in a phosphate buffered saline, and the resultant solution was subjected to a GFC analysis. As a result, the copolymer 2 had a weight-average molecular weight of 22,000 in terms of polyethylene glycol. The GFC analysis was carried out under the same conditions as Synthesis Example 1.

Synthesis Example 3 (Synthesis of Copolymer 3)

4.7 g of MPC and 5.3 g of BMA were weighed and introduced into a glass flask for polymerization. 0.244 g of AIBN was added thereto as a polymerization initiator, and 27.0 g of a purified water and 63.0 g of ethanol were further added thereto as polymerization solvents. Thus, the mole ratio of the monomers MPC/BMA was 30/70. The internal air in the reaction container was sufficiently replaced with nitrogen, and then the monomers were polymerized under heating at 55° C. for 5 hours. The resultant reaction liquid was cooled with ice, and was added to diethyl ether dropwise to precipitate the product. The precipitate was isolated by filtration, washed with diethyl ether, and dried under vacuum, to obtain a white powder of the copolymer 3.

The obtained copolymer 3 was dissolved in a phosphate buffered saline, and the resultant solution was subjected to a GFC analysis. As a result, the copolymer 3 had a weight-average molecular weight of 93,000 in terms of polyethylene glycol. The GFC analysis was carried out under the same conditions as Synthesis Example 1.

Synthesis Example 4 (Synthesis of Copolymer 4)

6.0 g of MPC and 4.0 g of MAc were weighed and introduced into a glass flask for polymerization. 0.78 g of AIBN was added thereto as a polymerization initiator, and 90.0 g of a purified water was further added thereto as a polymerization solvent. Thus, the mole ratio of the monomers MPC/MAc was 30/70. The internal air in the reaction container was sufficiently replaced with nitrogen, and then the monomers were polymerized under heating at 70° C. for 6 hours. The resultant reaction liquid was cooled with ice, and was added to diethyl ether dropwise to precipitate the product. The precipitate was isolated by filtration, washed with diethyl ether, and dried under vacuum, to obtain a white powder of the copolymer 4.

The obtained copolymer 4 was dissolved in a phosphate buffered saline, and the resultant solution was subjected to a GFC analysis. As a result, the copolymer 4 had a weight-average molecular weight of 680,000 in terms of polyethylene glycol. The GFC analysis was carried out under the same conditions as Synthesis Example 1.

The monomer mole ratios and the weight-average molecular weights of Synthesis Examples 1 to 4 are shown in Table 1.

<Evaluation Test of Protein Stabilization Effect Under Room-Temperature Storage Condition>

The copolymers 1 and 2 were used to prepare protein stabilization reagents of Examples 1-1 to 1-4. The copolymers 3 and 4 were used to prepare protein stabilization reagents of Comparative Examples 1-1 and 1-2. Furthermore, a protein stabilizer different from the copolymers was used to prepare protein stabilization reagents of Comparative Examples 1-3 and 1-4. No protein stabilizers were used to prepare a protein-containing solution of Comparative Example 1-5. Also the protein-containing solution of Comparative Example 1-5 is referred to as the protein stabilization reagent for convenience.

The protein stabilization effects of the protein stabilization reagents under a room-temperature storage condition were evaluated in the following manner.

Example 1-1

Preparation of Protein Stabilization Reagent

A horseradish peroxidase-labeled goat anti-mouse immunoglobulin G antibody (CAT NO. 170-6516, available from Bio-Rad, hereinafter referred to as POD-IgG) was dissolved in a Dulbecco's phosphate buffered saline (CAT NO. D1408, available from Sigma-Aldrich) in such a manner that the final concentration was 0.005% by volume, and an aqueous solution containing 5% by mass of the copolymer 1 was dissolved therein in such a manner that the final concentration was 50% by volume (the concentration of the copolymer 1 in the final product solution was about 2.5 w/v %), to prepare the protein stabilization reagent. In the present invention, the term "w/v %" is "(mass/volume) %", which means the mass (g) of a component in 100 ml of a solution. For example, the phrase "a solution contains 1.0 w/v % of a copolymer" means that 100 ml of the solution contains 1.0 g of the copolymer.

Evaluation Test of Protein Stabilization Effect

The above prepared protein stabilization reagent was incubated (stored) at 25° C. The protein stabilization effect of the protein stabilization reagent was evaluated by the following test method on the incubation start date (before the incubation) and after the incubation for 1, 3, and 6 days.

On the incubation start date or after the incubation for 1, 3, or 6 days, the protein stabilization reagent was added to a polystyrene 96-well microplate at 8 μL/well. A 3,3',5,5'-tetramethylbenzidine (TMB) solution (CAT NO. 50-76, available from KPL) was added thereto at 100 μL/well, so that a chromogenic reaction of POD-IgG (protein) was carried out for 7 minutes. Then, a 2-N sulfuric acid was added to the resultant at 50 μL/well to stop the chromogenic reaction. The absorbance of the resulting reaction liquid was measured with respect to a light having a wavelength of 450 nm, to evaluate the effect of stabilizing POD-IgG (the protein stabilization effect).

TABLE 1

| | | | Synthesis Example 1 Copolymer 1 | Synthesis Example 2 Copolymer 2 | Synthesis Example 3 Copolymer 3 | Synthesis Example 4 Copolymer 4 |
|---|---|---|---|---|---|---|
| Monomer mole ratio (% by mole) | Monomer (a) | MPC | 40 | 40 | 30 | 30 |
| | Monomer (b) | GLM | 40 | 20 | — | — |
| | Monomer (c) | BMA | 20 | 40 | 70 | — |
| | Monomer (x) | MAc | — | — | — | 70 |
| Weight-average molecular weight (Mw) | | | 98,000 | 22,000 | 93,000 | 680,000 |

Specifically, the absorbance values were measured by the following method on the incubation start date (immediately after the preparation of the protein stabilization reagent) and after the incubation for the days. The enzymatic activity retention rates (%) were calculated using the following mathematical formula [1]. The protein stabilization effects were evaluated based on the enzymatic activity retention rates (%). A higher enzymatic activity retention rate corresponds to a higher protein stabilization effect. Incidentally, the enzymatic activity retention rate on the incubation start date is 100% because the denominator and numerator of the mathematical formula [1] are both the absorbance value measured on the incubation start date. Furthermore, also the high activity duration period (days) of the protein stabilization reagent, for which the reagent could maintain 80% or more of an enzymatic activity retention rate, was evaluated. The measurement results of the enzymatic activity retention rates and the high activity duration period are shown in Table 2.

Absorbance Measurement Method

The absorbance values of the protein stabilization reagent for calculating the enzymatic activity retention rate using the following mathematical formula [1] were measured by using Spectra Max M3 (available from Molecular Devices) under the condition of endpoint wavelength 450 nm.

$$\text{Enzymatic activity retention rate (\%)} = \frac{\text{Absorbance value of protein stabilization reagent after days of incubation}}{\text{Absorbance value of protein stabilization reagent on incubation start date}} \times 100 \quad [1]$$

Example 1-2

The protein stabilization reagent of Example 1-2 was prepared and evaluated in the same manner as Example 1-1 except that the aqueous solution containing 5% by mass of the copolymer 1 was dissolved in such a manner that the final concentration was 10% by volume (the concentration of the copolymer 1 in the final product solution was about 0.5 w/v %). The results are shown in Table 2.

Example 1-3

The protein stabilization reagent of Example 1-3 was prepared and evaluated in the same manner as Example 1-1 except that an aqueous solution containing 5% by mass of the copolymer 2 was used instead of the aqueous solution containing 5% by mass of the copolymer 1. The results are shown in Table 2.

Example 1-4

The protein stabilization reagent of Example 1-4 was prepared and evaluated in the same manner as Example 1-1 except that an aqueous solution containing 5% by mass of the copolymer 2 was dissolved instead of the aqueous solution containing 5% by mass of the copolymer 1 in such a manner that the final concentration was 10% by volume (the concentration of the copolymer 2 in the final product solution was about 0.5 w/v %). The results are shown in Table 2.

Comparative Example 1-1

The protein stabilization reagent of Comparative Example 1-1 was prepared and evaluated in the same manner as Example 1-1 except that an aqueous solution containing 5% by mass of the copolymer 3 was used instead of the aqueous solution containing 5% by mass of the copolymer 1. The results are shown in Table 2.

Comparative Example 1-2

The protein stabilization reagent of Comparative Example 1-2 was prepared and evaluated in the same manner as Example 1-1 except that an aqueous solution containing 5% by mass of the copolymer 4 was used instead of the aqueous solution containing 5% by mass of the copolymer 1. The results are shown in Table 2.

Comparative Example 1-3

The protein stabilization reagent of Comparative Example 1-3 was prepared and evaluated in the same manner as Example 1-1 except that sucrose was used instead of the aqueous solution containing 5% by mass of the copolymer 1 in such a manner that the final concentration was 10 w/v %. The results are shown in Table 2.

Comparative Example 1-4

The protein stabilization reagent of Comparative Example 1-4 was prepared and evaluated in the same manner as Example 1-1 except that an aqueous solution containing 5% by mass of BSA was used instead of the aqueous solution containing 5% by mass of the copolymer 1. The results are shown in Table 2.

Comparative Example 1-5

Only POD-IgG was added to the Dulbecco's phosphate buffered saline, and a purified water was added thereto to adjust the final POD-IgG concentration at 0.005% by volume, to prepare the protein stabilization reagent of Comparative Example 1-5. The protein stabilization reagent of Comparative Example 1-5 was evaluated in the same manner as Example 1-1. The results are shown in Table 2.

TABLE 2

| | Enzymatic activity retention rate (%) | | | | High activity duration period (days) |
|---|---|---|---|---|---|
| | Start date | 1 day after | 3 days after | 6 days after | |
| Example 1-1 | 100 | 93 | 94 | 90 | 6 |
| Example 1-2 | 100 | 87 | 88 | 89 | 6 |
| Example 1-3 | 100 | 95 | 92 | 83 | 6 |
| Example 1-4 | 100 | 90 | 87 | 82 | 6 |
| Comp. Ex. 1-1 | 100 | 79 | 64 | 54 | 0 |
| Comp. Ex. 1-2 | 100 | 78 | 65 | 52 | 0 |
| Comp. Ex. 1-3 | 100 | 12 | 7 | 2 | 0 |
| Comp. Ex. 1-4 | 100 | 73 | 62 | 46 | 0 |
| Comp. Ex. 1-5 | 100 | 12 | 3 | 1 | 0 |

As is clear from Table 2, the protein stabilization reagents of Examples 1-1 to 1-4 were significantly superior to those of Comparative Examples 1-1 to 1-5 in the effect of stabilizing the protein (POD-IgG) during the storage at the room temperature. Although the enzymatic activity retention rates of some samples were slightly increased with incubation time, the results were considered as being obtained due to small measurement errors.

<Evaluation Test of Protein Stabilization Effect Under Refrigeration-Temperature Storage Condition>

The protein stabilization reagents of further examples were prepared, and the protein stabilization effects of the reagents under a refrigeration-temperature storage condition were evaluated in the following manner.

Example 2-1

The protein stabilization reagent of Example 2-1 was prepared in the same manner as Example 1-1 except that the aqueous solution containing 5% by mass of the copolymer 1 was dissolved in such a manner that the final concentration was 10% by volume (the concentration of the copolymer 1 in the final product solution was about 0.5 w/v %). The protein stabilization reagent of Example 2-1 was evaluated in the same manner as Example 1-1 except that the reagent was incubated (stored) at 4° C., and the protein stabilization effect of the reagent was measured on the incubation start date and after the incubation for 1, 2, 4, 8, 15, 30, and 60 weeks. The results are shown in Table 3. It should be noted that the high activity duration period is expressed in "weeks" in the evaluation test under the refrigeration-temperature storage condition.

Example 2-2

The protein stabilization reagent of Example 2-2 was prepared and evaluated in the same manner as Example 2-1 except that the aqueous solution containing 5% by mass of the copolymer 1 was dissolved in such a manner that the final concentration was 2% by volume (the concentration of the copolymer 1 in the final product solution was about 0.1 w/v %). The results are shown in Table 3.

Example 2-3

The protein stabilization reagent of Example 2-3 was prepared and evaluated in the same manner as Example 2-1 except that the aqueous solution containing 5% by mass of the copolymer 2 was dissolved in such a manner that the final concentration was 10% by volume (the concentration of the copolymer 2 in the final product solution was about 0.5 w/v %). The results are shown in Table 3.

Example 2-4

The protein stabilization reagent of Example 2-4 was prepared and evaluated in the same manner as Example 2-1 except that the aqueous solution containing 5% by mass of the copolymer 2 was dissolved in such a manner that the final concentration was 2% by volume (the concentration of the copolymer 2 in the final product solution was about 0.1 w/v %). The results are shown in Table 3.

Example 2-5

The protein stabilization reagent of Example 2-5 was prepared and evaluated in the same manner as Example 2-1 except that the aqueous solution containing 5% by mass of the copolymer 2 was dissolved in such a manner that the final concentration was 2% by volume (the concentration of the copolymer 2 in the final product solution was about 0.1 w/v %) and except that sucrose was dissolved in such a manner that the final concentration was 10% by volume. The results are shown in Table 3.

Comparative Examples 2-1 to 2-5

The protein stabilization reagents of Comparative Examples 2-1 to 2-5 were prepared in the same manner as Comparative Examples 1-1 to 1-5 respectively, and were evaluated in the same manner as Example 2-1. The results are shown in Table 3.

TABLE 3

| | Enzymatic activity retention rate (%) | | | | | | | | High activity duration period (weeks) |
|---|---|---|---|---|---|---|---|---|---|
| | Start date | 1 week after | 2 weeks after | 4 weeks after | 8 weeks after | 15 weeks after | 30 weeks after | 60 weeks after | |
| Ex. 2-1 | 100 | 94 | 100 | 83 | 82 | 91 | 84 | 82 | 60 |
| Ex. 2-2 | 100 | 85 | 90 | 87 | 85 | 82 | 81 | 75 | 30 |
| Ex. 2-3 | 100 | 92 | 97 | 80 | 80 | 86 | 82 | 79 | 30 |
| Ex. 2-4 | 100 | 82 | 89 | 85 | 81 | 83 | 80 | 69 | 30 |
| Ex. 2-5 | 100 | 86 | 89 | 88 | 89 | 90 | 85 | 90 | 60 |
| Comp. Ex. 2-1 | 100 | 83 | 76 | 46 | 32 | 16 | 4 | 1 | 1 |
| Comp. Ex. 2-2 | 100 | 80 | 70 | 56 | 39 | 42 | 17 | 23 | 1 |
| Comp. Ex. 2-3 | 100 | 3 | 1 | 4 | 0 | 0 | 1 | 0 | 0 |
| Comp. Ex. 2-4 | 100 | 97 | 96 | 66 | 46 | 28 | 8 | 0 | 2 |
| Comp. Ex. 2-5 | 100 | 7 | 4 | 5 | 2 | 1 | 0 | 0 | 0 |

As is clear from Table 3, the protein stabilization reagents of Examples 2-1 to 2-5 were significantly superior to those of Comparative Examples 2-1 to 2-5 in the effect of stabilizing the protein (POD-IgG) during the storage at the refrigeration temperature. Although the enzymatic activity retention rates of some samples were slightly increased with incubation time, the results were considered as being obtained due to small measurement errors.

INDUSTRIAL APPLICABILITY

The protein stabilizer of the present invention and the protein stabilization reagent containing the protein stabilizer can be used for biochemical assays and the like such as enzyme immunoassays, turbidimetric immunoassays, nucleic acid assays, and immunostaining assays, in the fields where it is necessary to stably maintain a bioactivity of a protein, preferably in the fields of clinical examinations, in-vitro diagnostics, companion diagnostics, food analyses, environment analyses, etc. Furthermore, other than above, the protein stabilizer and the protein stabilization reagent are expected to be used in various fields of medical instruments, pharmaceuticals, biosensing technologies, etc.

What is claimed is:

1. A protein stabilization solution consisting of a protein, water, a buffer solution and a protein stabilizer,
    wherein the protein is at least one selected from the group consisting of antibodies, peroxidases, alkaline phosphatases, β-D-galactosidases, lipases, DNA polymerases, RNA polymerases, reverse transcriptases, and complexes of an antibody and an enzyme,
    wherein the protein stabilizer is a copolymer prepared by copolymerizing a monomer (a), a monomer (b), and a monomer (c),
    wherein
    the monomer (a) is represented by the following formula (1):

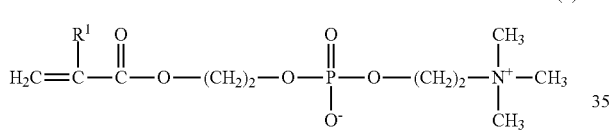

(1)

wherein $R^1$ is a hydrogen atom or a methyl group, the monomer (b) is represented by the following formula (2):

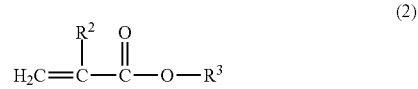

(2)

wherein $R^2$ is a hydrogen atom or a methyl group, and $R^3$ is an alkyl group
    that contains 3 to 6 carbon atoms and has 2 or more hydroxyl groups, and the monomer (c) is represented by the following formula (3):

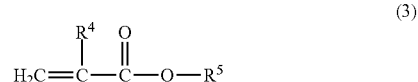

(3)

wherein $R^4$ is a hydrogen atom or a methyl group, and $R^5$ is an alkyl group containing 2 to 18 carbon atoms, and
    wherein the content of the protein stabilizer in the protein stabilization solution is 0.01% to 5.0% by mass.

2. A method for stabilizing a protein, comprising making the protein coexist in a solution consisting of water, the buffer solution and the protein stabilizer according to claim 1,
    wherein the protein is at least one selected from the group consisting of antibodies, peroxidases, alkaline phosphatases, β-D-galactosidases, lipases, DNA polymerases, RNA polymerases, reverse transcriptases, and complexes of an antibody and an enzyme, wherein the content of the protein stabilizer is 0.01% to 5.0% by mass in the solution coexisting with the protein.

* * * * *